(12) United States Patent
Okoniewski

US008900135B2

(10) Patent No.: US 8,900,135 B2
(45) Date of Patent: Dec. 2, 2014

(54) SINGLE INCISION DEPLOYABLE PLATFORM

(75) Inventor: Gregory G. Okoniewski, North Haven, CT (US)

(73) Assignee: Covidien LP, Mansfield, MA (US)

( * ) Notice: Subject to any disclaimer, the term of this patent is extended or adjusted under 35 U.S.C. 154(b) by 227 days.

(21) Appl. No.: 13/412,102

(22) Filed: Mar. 5, 2012

(65) Prior Publication Data

US 2012/0253133 A1 Oct. 4, 2012

Related U.S. Application Data

(60) Provisional application No. 61/469,023, filed on Mar. 29, 2011.

(51) Int. Cl.
*A61B 1/32* (2006.01)
*A61B 17/58* (2006.01)
*A61B 17/60* (2006.01)
*A61F 2/00* (2006.01)
*A61B 19/00* (2006.01)
*A61B 1/00* (2006.01)
*A61B 17/34* (2006.01)
*A61B 17/29* (2006.01)

(52) U.S. Cl.
CPC ..... *A61B 1/00135* (2013.01); *A61B 2017/3466* (2013.01); *A61B 17/3423* (2013.01); *A61B 2017/2906* (2013.01); *A61B 17/29* (2013.01); *A61B 19/5212* (2013.01)
USPC .............................. 600/204; 606/99; 606/130

(58) Field of Classification Search
CPC ..................................................... A61B 19/22
USPC ..................... 606/281, 99, 130; 600/204
See application file for complete search history.

(56) References Cited

U.S. PATENT DOCUMENTS

| | | | | |
|---|---|---|---|---|
| 2,898,917 | A * | 8/1959 | Wallace | 604/180 |
| 3,628,535 | A * | 12/1971 | Ostrowsky et al. | 604/303 |
| 4,593,681 | A * | 6/1986 | Soni | 600/102 |
| 5,269,772 | A | 12/1993 | Wilk | |
| 5,275,610 | A * | 1/1994 | Eberbach | 606/198 |
| 5,289,817 | A * | 3/1994 | Williams et al. | 600/204 |
| 5,318,013 | A | 6/1994 | Wilk | |
| 5,582,577 | A * | 12/1996 | Lund et al. | 600/204 |
| 5,613,939 | A * | 3/1997 | Failla | 600/201 |
| 5,735,842 | A * | 4/1998 | Krueger et al. | 606/1 |
| 5,947,970 | A * | 9/1999 | Schmelzeisen et al. | 606/70 |
| 5,957,927 | A * | 9/1999 | Magee et al. | 606/99 |
| 6,530,926 | B1 * | 3/2003 | Davison | 606/279 |
| 6,605,037 | B1 * | 8/2003 | Moll et al. | 600/204 |
| 6,699,235 | B2 * | 3/2004 | Wallace et al. | 606/1 |
| 8,685,077 | B2 * | 4/2014 | Laske et al. | 623/1.11 |
| 2003/0208203 | A1 * | 11/2003 | Lim et al. | 606/61 |
| 2005/0065409 | A1 * | 3/2005 | de la Torre et al. | 600/204 |
| 2005/0234294 | A1 | 10/2005 | Saadat et al. | |

(Continued)

*Primary Examiner* — David Bates

(57) ABSTRACT

A surgical triangulation device and method of use is disclosed. The surgical triangulation device includes an elongate member, the elongate member defining a longitudinal axis and being adapted for insertion through a surgical access portal. The surgical triangulation device also includes a platform pivotably attached near a distal end of the elongate member, the platform defining a plurality of lumens and a central opening therethrough. The platform has a first position, where a first end of the platform is positioned proximate to the elongate member and a second end of the platform extends distally past a distal end of the elongate member, and a second position, where the platform is nearly orthogonal to the longitudinal axis.

14 Claims, 13 Drawing Sheets

(56) References Cited

U.S. PATENT DOCUMENTS

| | | |
|---|---|---|
| 2007/0167680 A1 | 7/2007 | Miyamoto et al. |
| 2008/0188868 A1 | 8/2008 | Weitzner et al. |
| 2008/0221591 A1* | 9/2008 | Farritor et al. ............ 606/130 |
| 2009/0012477 A1 | 1/2009 | Norton et al. |
| 2010/0240960 A1 | 9/2010 | Richard |

* cited by examiner

SINGLE INCISION DEPLOYABLE PLATFORM

CROSS REFERENCE TO RELATED APPLICATIONS

The present application claims the benefit of and priority to U.S. Provisional Application Ser. No. 61/469,023, filed on Mar. 29, 2011, the entire contents of which are incorporated herein by reference.

BACKGROUND

1. Technical Field

The present disclosure relates generally to surgical instruments for use with a seal anchor member. More particularly, the present disclosure relates to articulating surgical instruments usable with a seal anchor member that provides multiple instrument access through a single incision in a minimally invasive surgical procedure.

2. Description of Related Art

Increasingly, many surgical procedures are performed through small incisions in the skin. As compared to the larger incisions typically required in traditional procedures, smaller incisions result in less trauma to the patient. By reducing the trauma to the patient, the time required for recovery is also reduced. Generally, the surgical procedures that are performed through small incisions in the skin are referred to as endoscopic. If the procedure is performed on the patient's abdomen, the procedure is referred to as laparoscopic. Throughout the present disclosure, the term minimally invasive is to be understood as encompassing both endoscopic and laparoscopic procedures.

During a typical minimally invasive procedure, surgical objects, such as surgical access devices (e.g., trocar and cannula assemblies) or endoscopes, are inserted into the patient's body through the incision in tissue. In general, prior to the introduction of the surgical object into the patient's body, insufflation gas is used to enlarge the area surrounding the target surgical site to create a larger, more accessible work area. Accordingly, the maintenance of a substantially fluid-tight seal is desirable so as to inhibit the escape of the insufflation gas and the deflation or collapse of the enlarged surgical site. In response to this, various access devices with sealing features are used during the course of minimally invasive procedures to provide an access for surgical objects to enter the patient's body. Each of these devices is configured for use through a single incision or a naturally occurring orifice (i.e. mouth, anus, or vagina) while allowing multiple instruments to be inserted through the device to access the working space beyond the device.

During procedures employing multiple surgical instruments through a single incision access device, it is advantageous to determine the position of the end effectors relative to each other and/or relative to a fixed reference point. This is desirable when one or more of the instruments includes an end effector that is articulable relative to the surgical instrument. Identifying the position of each end effector relative to the other end effectors and/or a common reference point is advantageous during a surgical procedure.

One example, as disclosed by U.S. Publication No. 2005/0234294, uses an articulating element disposed near a distal region and pivotally coupled to hinges by linkages.

Another example, as disclosed by U.S. Publication Nos. 2007/0167680 and US2008/0051631, uses a rod connected to linking members which spread a set of arm members containing surgical devices apart when the rod is actuated.

Another example, as disclosed by U.S. Publication No. 2008/0188868, uses a collar, a wedge, a balloon or bands to help maintain a divergence between the surgical devices.

Yet another example, as disclosed by U.S. Pat. Nos. 5,318,013; 5,395,367; and 5,511,564, uses an actuator including an articulated linking comprising a pair of arms pivotably connected to a push rod and to shafts of respective grasping forceps to enable relative spreading of the grasping forceps from a straightened or mutually parallel configuration to a spread use configuration.

However, a continuing need exists for determining the relative positions of the end effectors of articulating surgical instruments used with an access device that permits multiple instruments to be used through a single incision or orifice.

SUMMARY

A surgical triangulation device and method of use is disclosed. The surgical triangulation device includes an elongate member, the elongate member defining a longitudinal axis and being adapted for insertion through a surgical access portal. The surgical triangulation device also includes a platform pivotably attached near a distal end of the elongate member, the platform defining a plurality of lumens and a central opening therethrough. The platform has a first position, where a first end of the platform is positioned proximate to the elongate member and a second end of the platform extends distally past a distal end of the elongate member, and a second position, where the platform is nearly orthogonal to the longitudinal axis. Alternatively, the platform may be orthogonal to the longitudinal axis when in the second position. The plurality of lumens is adapted for the reception of surgical objects therethrough. One or more of the plurality of lumens may be disposed proximate to each of the first and second ends and the central opening may be dimensioned to allow a portion of the elongate member to project therethrough.

One or more of the plurality of lumens may include a locking member for securing surgical objects thereto and the platform is adapted to transition between the first and second positions upon actuation of the secured surgical object. Alternatively, the platform is adapted to transition between the first and second positions upon actuation of at least one actuating member attached thereto and extending proximally therefrom. The at least one actuating member may be in the form of a wire or wires or may instead be a rod.

The elongate member may further include a latch disposed near the distal end and the platform may further include a detent dimensioned for reception of the latch. The latch and the detent are adapted to secure the platform in the second position. The latch may be actuatable into and out of the detent by a cable or wire attached to the latch and extending proximally therefrom and the latch may be biased toward the detent by a spring-like mechanism.

The elongate member may include at least one passage adapted for the reception of a surgical object which may, for example, be a scope.

A surgical system including the surgical triangulation device is also disclosed and further includes a surgical access portal adapted for sealed insertion into an incision in tissue and defining at least one lumen therethrough. The surgical triangulation device includes an elongate member and a platform, defines a longitudinal axis and is adapted for insertion through the at least one lumen of the surgical access portal. The platform is pivotably attached near a distal end of the elongate member and defines a plurality of lumens and a central opening therethrough. The platform has a first position where a first end of the platform is proximate to the elongate member and a second end of the platform extends distally past a distal end of the elongate member and a second position where the platform is nearly orthogonal to the elongate member.

A method for deploying the surgical triangulation device is also disclosed. The method includes the steps of providing a surgical access portal defining at least one lumen therethrough and adapted for sealed insertion into an incision in tissue, providing a surgical triangulation device including an elongate member and a platform as described above, transitioning the platform to the first position, inserting the surgical triangulation device through the at least one lumen of the surgical access portal and transitioning the platform to the second position.

The method may further include the step of securing a surgical object in place by actuating the locking member and may further include the step of actuating the latch, whereby the platform is secured in the second position.

BRIEF DESCRIPTION OF THE DRAWINGS

The accompanying drawings, which are incorporated in and constitute a part of this specification, illustrate embodiments of the invention, and together with a general description of the invention given above, and the detailed description of the embodiments given below, serve to explain the principles of the invention.

DETAILED DESCRIPTION

Figure 1:
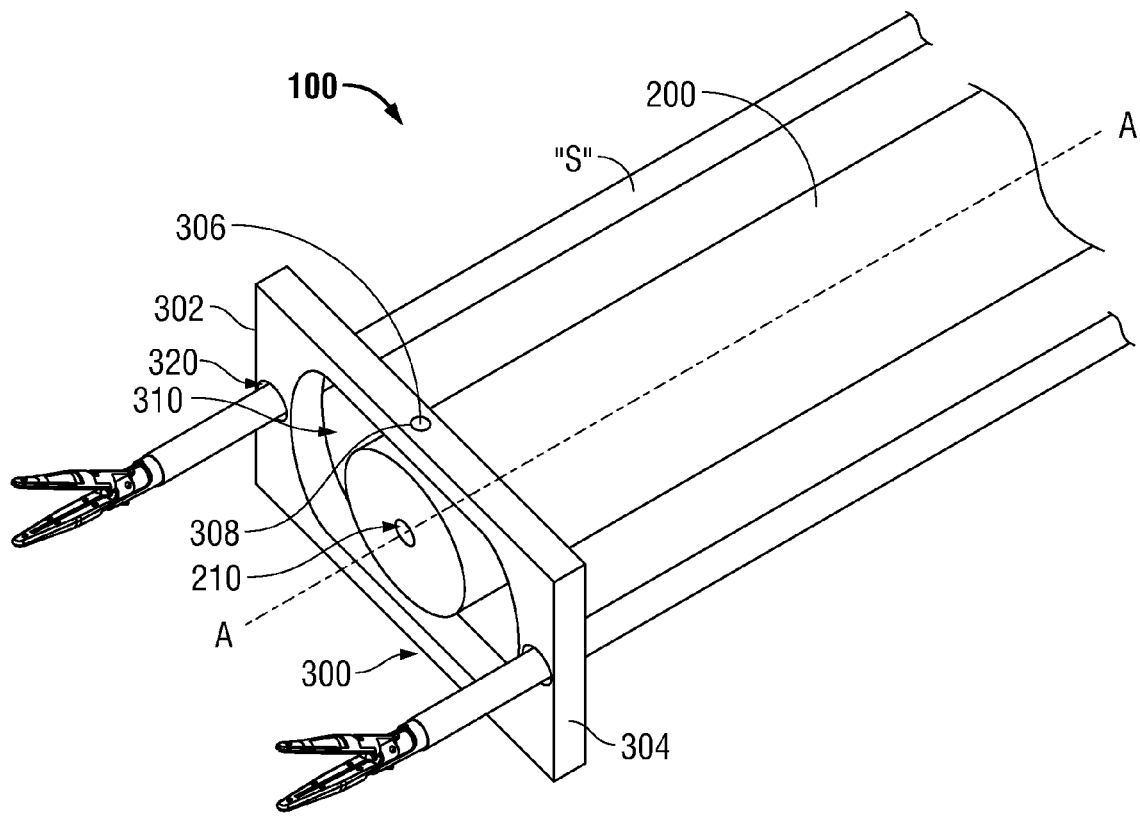
FIG. 1 is a perspective view of a surgical triangulation device in accordance with the present disclosure.

Disclosed herein is a surgical triangulation device for providing triangulation of surgical objects through a surgical access portal. More specifically a surgical triangulation device is disclosed which is capable of providing knowable and repeatable starting locations for multiple surgical objects through a single incision or orifice in a body.

Particular embodiments of the presently disclosed surgical device are described in detail with reference to the drawing figures wherein like reference numerals identify similar or identical elements. As used herein, the term "distal" refers to that portion which is farther from the user while the term "proximal" refers to that portion which is closer to the user or surgeon.

Figure 2:
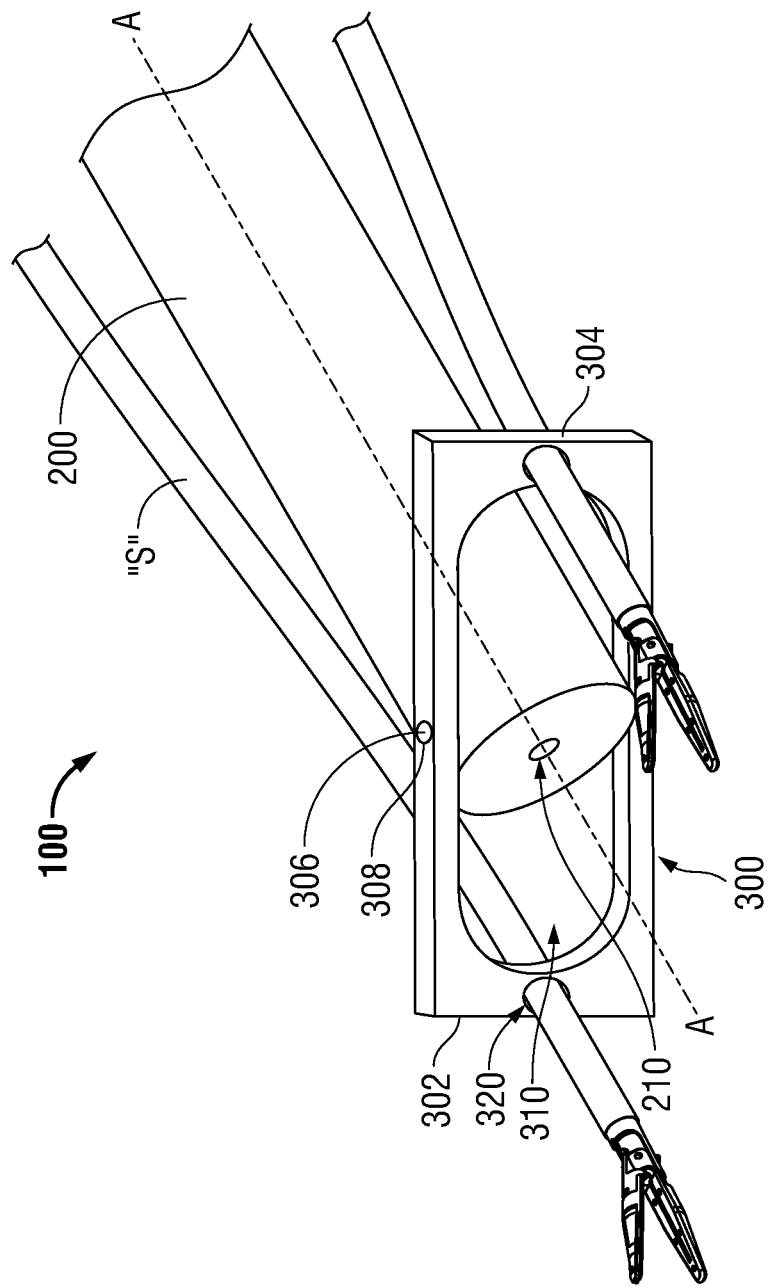
FIG. 2 is a perspective view of the surgical triangulation device of FIG. 1 when in the insertion position.

Referring now to FIGS. 1 and 2, a surgical triangulation device 100 is disclosed including an elongate member 200 and a platform 300 pivotably attached near the distal end of elongate member 200. Surgical triangulation device 100 is adapted for insertion through a lumen and into a surgical site. The lumen may be in the form of a surgical access portal 400 (FIGS. 6-10), any naturally occurring orifice in the body, or an incision. Elongate member 200 defines a longitudinal axis A-A and may define one or more passages 210 adapted for the reception of surgical objects "S" therethrough in a substantially fluid sealed state. For example, passage 210 may receive an endoscope for providing the surgeon with an optical or video feed to aid in performing surgery.

Figure 3:
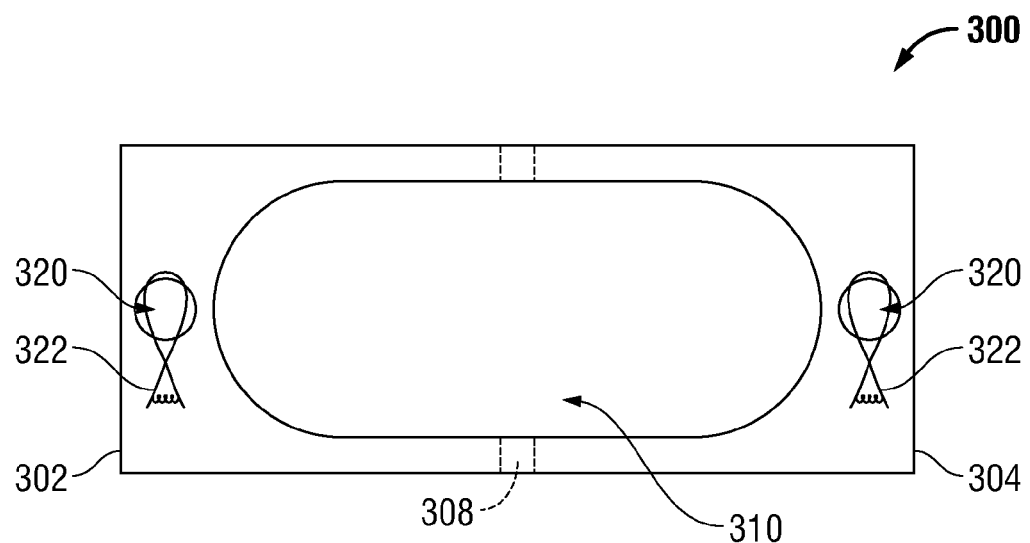
FIG. 3 is a top view of a platform of the surgical triangulation device of FIG. 1.
Figure 4:
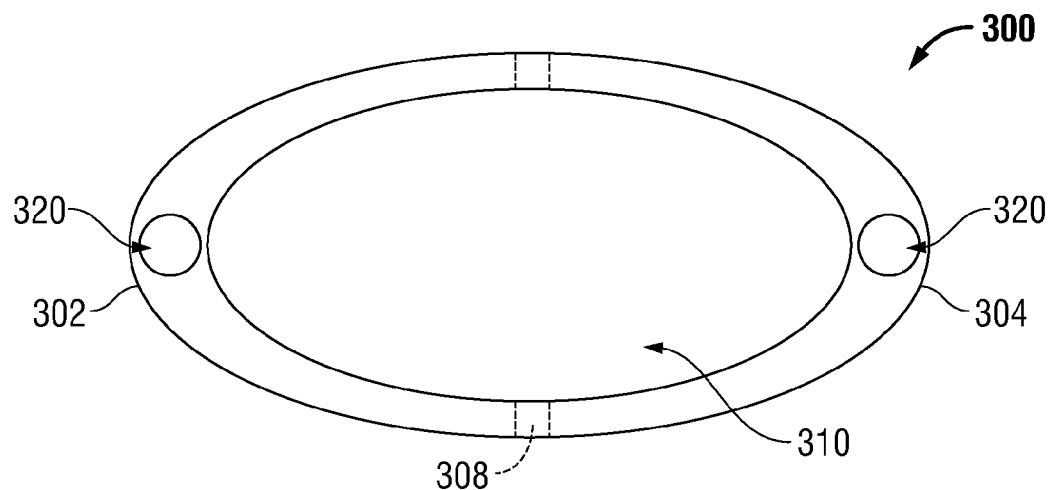
FIG. 4 is a top view of an alternate embodiment of the platform of FIG. 3.
Figure 5:
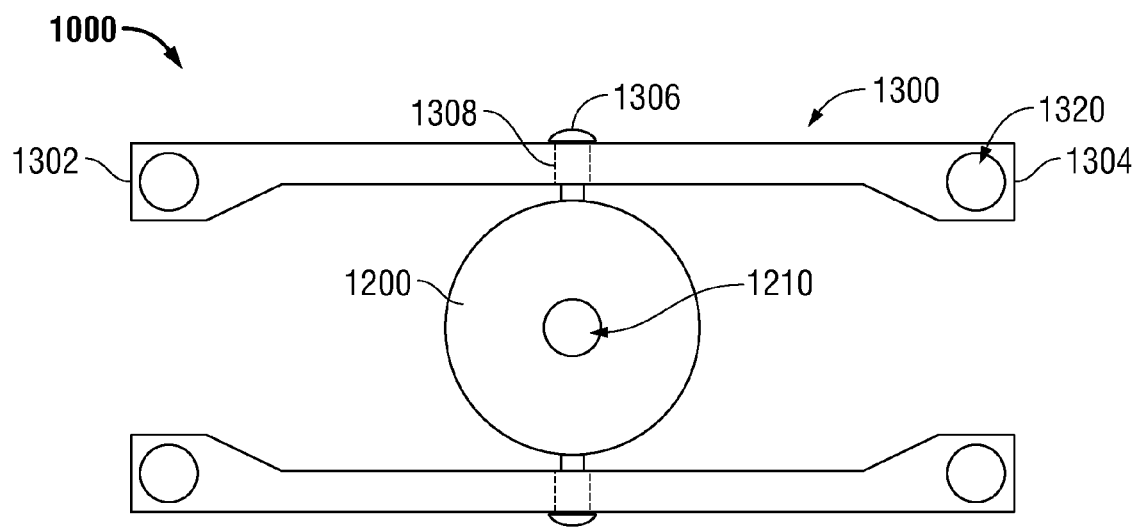
FIG. 5 is a bottom view of yet another embodiment of the platform of FIG. 3 including the elongate member and pins.
Figure 6:
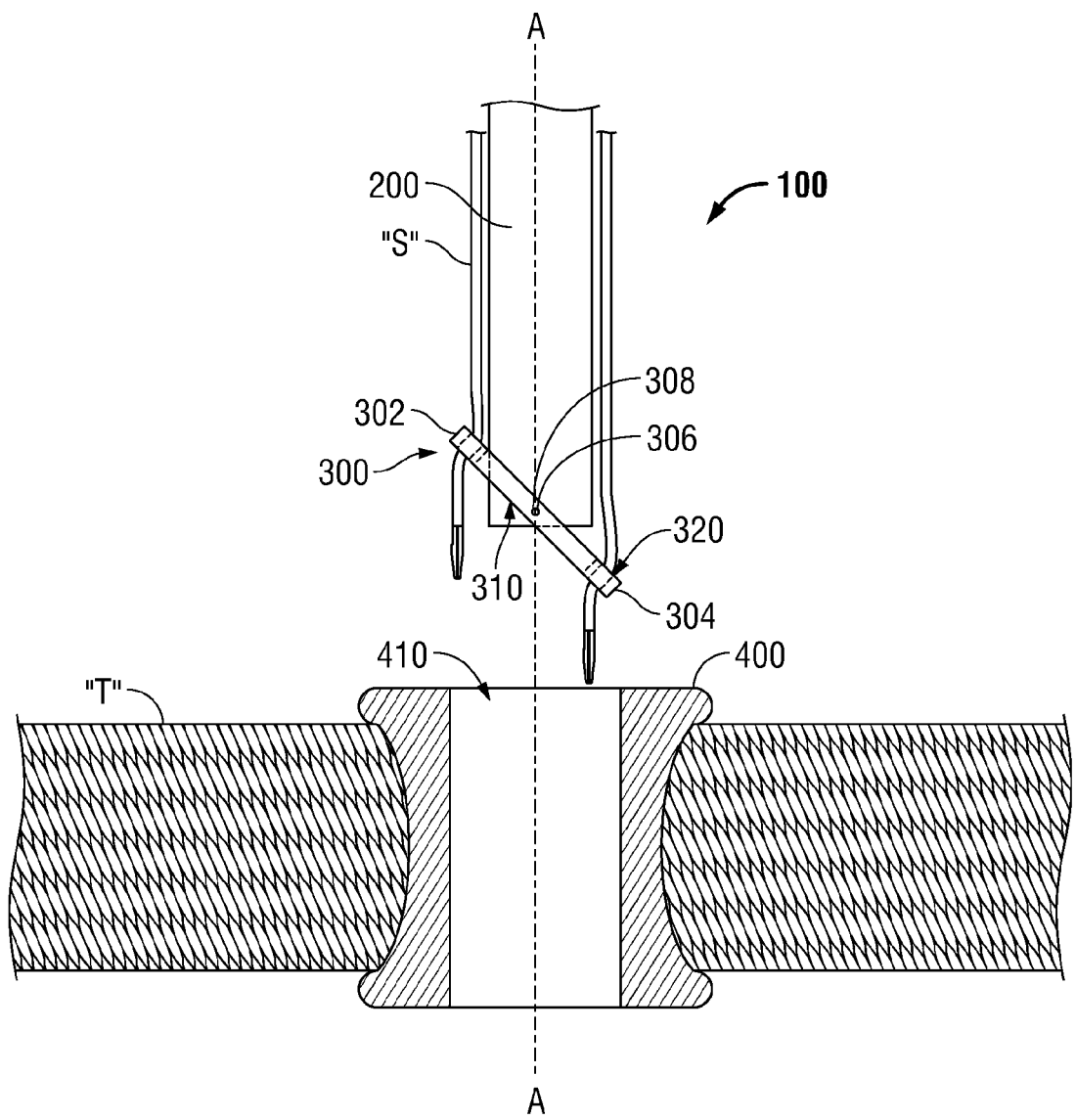
FIG. 6 is a side cut-away view of the surgical triangulation device of FIG. 1 prior to insertion through a surgical access portal.
Figure 7:
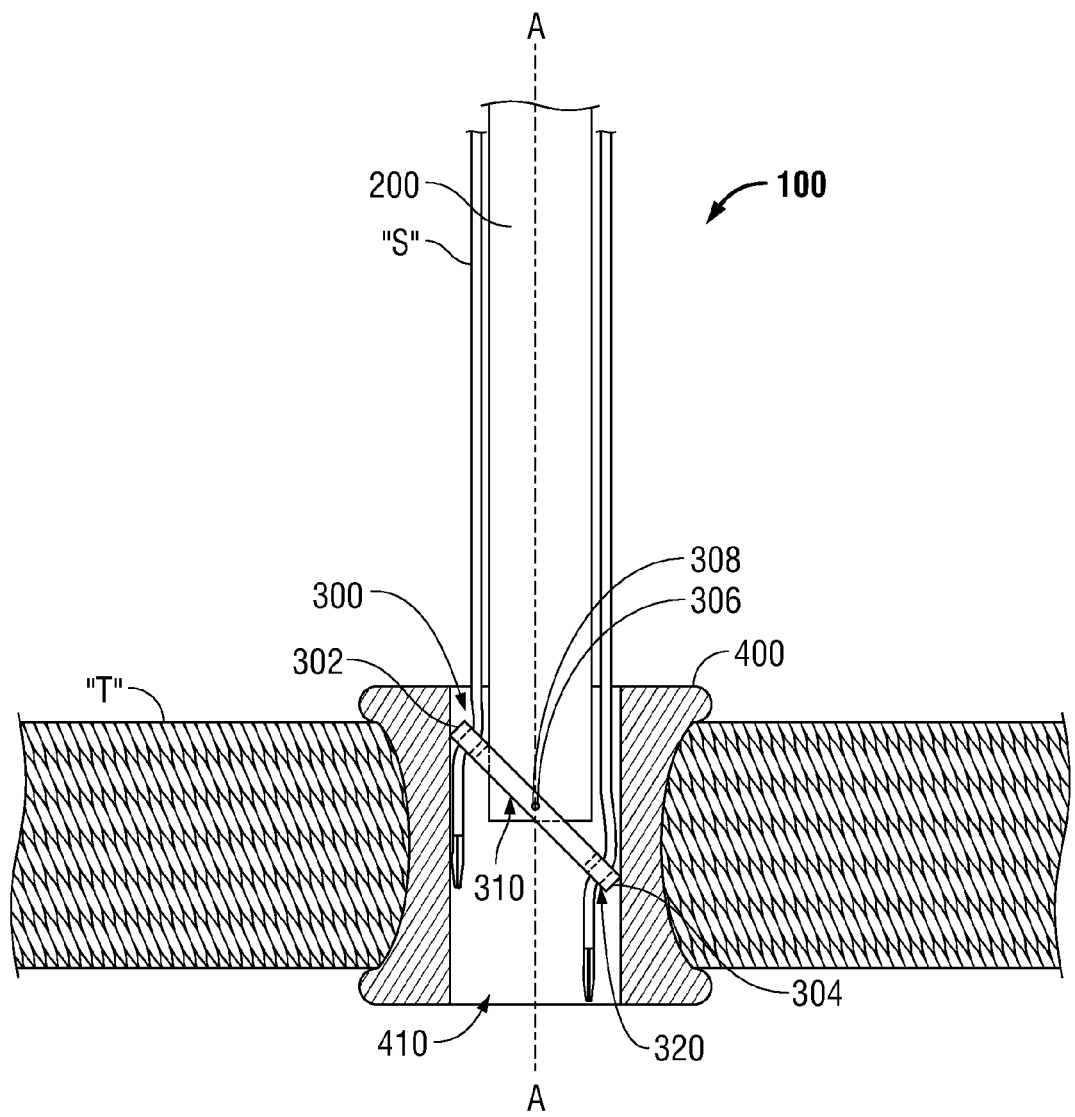
FIG. 7 is a side cut-away view of the surgical triangulation device of FIG. 1 during insertion through a surgical access portal.
Figure 8:
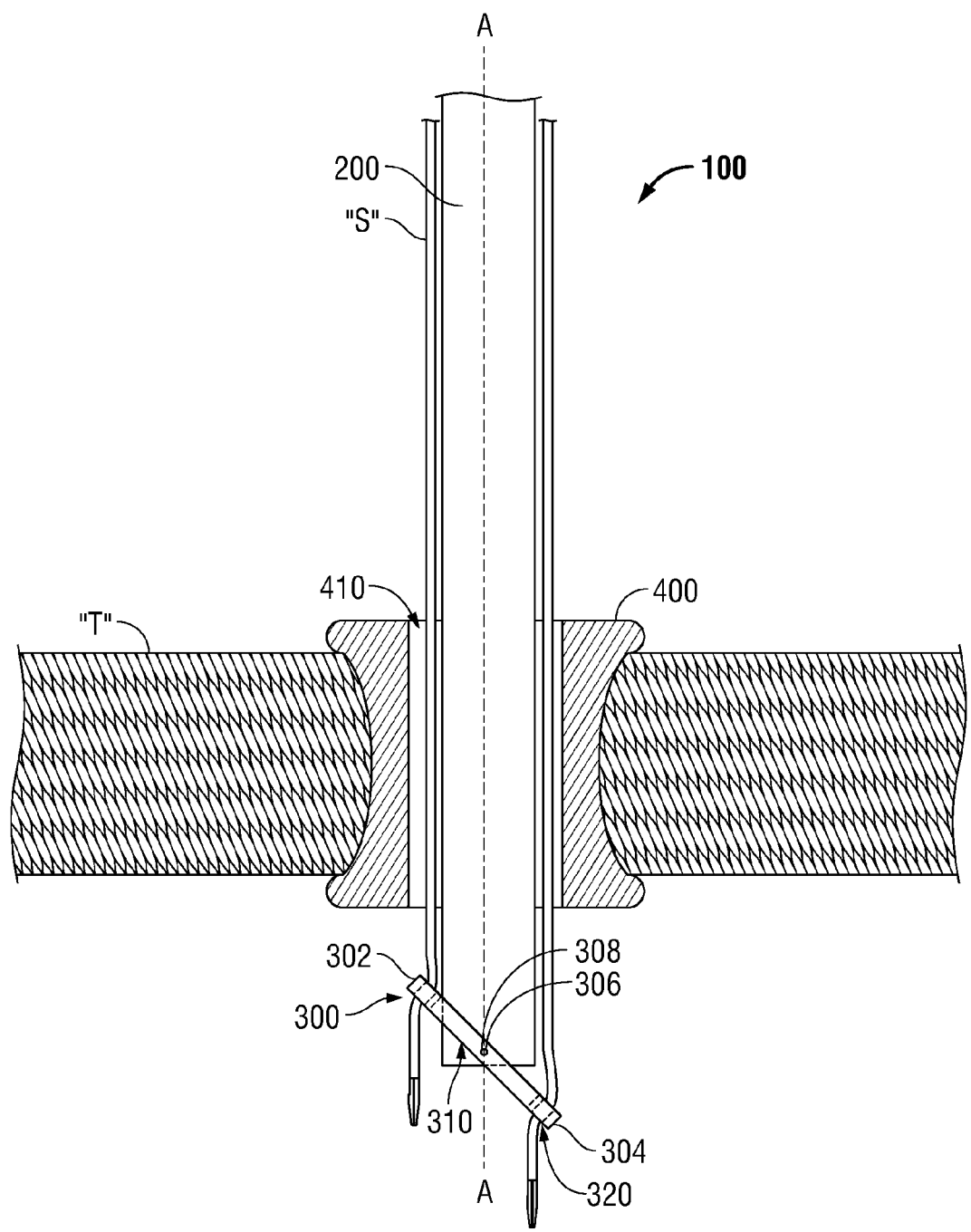
FIG. 8 is a side cut-away view of the surgical triangulation device of FIG. 1 after insertion through a surgical access portal.
Figure 9:
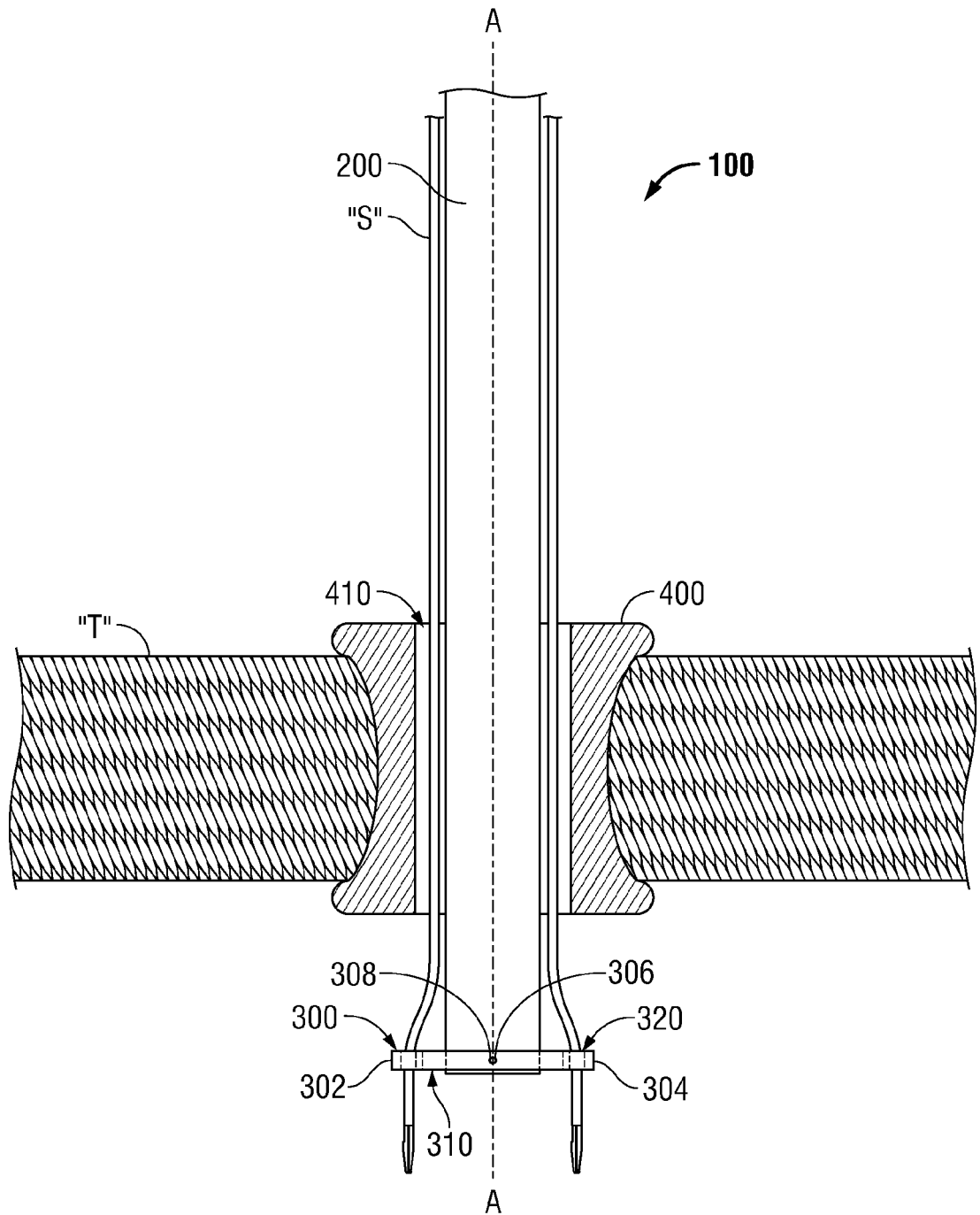
FIG. 9 is a side cut-away view of the surgical triangulation device of FIG. 8 with the platform in the deployed position.

Referring now to FIGS. 3-5, platform 300 includes a central opening 310 and two or more side lumens 320. Platform 300 defines a rectangular shape and two ends 302, 304. It is contemplated that platform 300 may be other shapes such as, for example, an oval (FIG. 4), a circle, a square, another polygonal shape or any other shape as known in the art. Central opening 310 is dimensioned to allow at least a portion of elongate member 200 to extend therethrough. Side lumens 320 are disposed proximate to each of ends 302 and 304, as seen in FIG. 3, and are adapted for the reception of surgical objects "S" therethrough. Side lumens 320 assist the surgeon with triangulation by providing knowable and repeatable starting positions for surgical objects "S" relative to platform 300 and elongate member 200. Platform 300 is attached to elongate member 200 by one or more pivot pins 306 at pivot points 308. Central opening 310 is generally oval shaped. It is contemplated, however, that central opening 310 may be any other shape such as, for example, a square, a circle or any other polygonal shape as needed, to allow platform 300 to pivot as close to parallel with longitudinal axis A-A as possible.

Referring now to FIGS. 6-9 and 11-12, platform 300 is pivotable about pivot points 308 between a deployed position, where platform 300 is orthogonal to longitudinal axis A-A of elongate member 200, and an insertion position, where one of ends 302 or 304 abuts or is proximate to elongate member 200 and the other end 302 or 304 extends distally past elongate member 200. The deployed position creates a separation or spacing between surgical objects "S" inserted through each of side lumens 320 and also between surgical objects "S" and elongate member 200. This allows a surgeon to utilize triangulation during surgery since surgical objects "S" will be able to approach the surgical site from different angles and directions. The insertion position, on the other hand, allows the cross-section of platform 300 to be reduced as much as possible for insertion of surgical triangulation device 100 through surgical access portal 400. It is contemplated that the insertion position may be achieved when either of ends 302 or 304 are abutting or proximate to elongate member 200, thus platform 300 may be pivoted in either direction to achieve the insertion position. Although two positions are disclosed it is contemplated that platform 300 may be actuated to any position within range of its rotational arc about pivot points 308 and within the physical limitations provided by contact between elongate member 200 and ends 302 and 304, respectively.

In another embodiment, referring now to FIG. 5, it is further contemplated that surgical triangulation device 1000 may instead include elongate member 1200 and two platforms 1300. Each platform 1300 is spaced apart from the other platform 1300 and defines a gap therebetween that is equal to or greater than the diameter of elongate member 1200. Each platform 1300 may include a side lumen 1320 proximate to each end 1302, 1304 and is separately attached to elongate member 1200 via its own pivot pin 1306. It is also contemplated that only one end 1302 or 1304 of each platform 1300 has a side lumen 1320. Having two platforms 1300 allows surgical triangulation device 1000 to achieve a smaller cross-section during insertion since each of platforms 1300 is able to align itself parallel to longitudinal axis A-A on either side of elongate member 1200. This is because ends 1302 and 1304 of platforms 1300 are not limited in their range of rotation about pivot pins 1306 by physical contact with elongate member 1200.

Referring now to FIGS. 6-9 and 11-12, platform 300 may be pivoted between the deployed and insertion positions through the manipulation of surgical objects "S" after surgical objects "S" have been inserted through side lumens 320 to a desired length. For example, friction between side lumens 320 and surgical objects "S" may allow a surgeon to pivot platform 300 without moving surgical objects "S" relative to side lumens 320. Surgical objects "S" may also include a portion that is slightly larger in diameter to facilitate a friction fit with side lumens 320 at the desired length. Alternatively, each side lumen 320 may include a locking member 322 for rigidly securing a surgical object "S" to side lumen 320 once the desired length of surgical object "S" has been inserted therethrough. Locking member 322 may be in the form of clamps, jaws, or other similar devices as known in the art and is shown in FIG. 3, for example, as a spring clamp. When one of surgical objects "S" is moved distally, the corresponding end 302 or 304 is rotated distally and the other end 302 or 304 is rotated proximally by virtue of platform 300 pivoting around pivot points 308. Alternatively, as seen in FIG. 10, a wire or rod 330 may be attached to platform 300 by a hinge 332 or other means of attachment such that manipulation of wire or rod 330 pivots platform 300 around pivot point 308.

Figure 10:
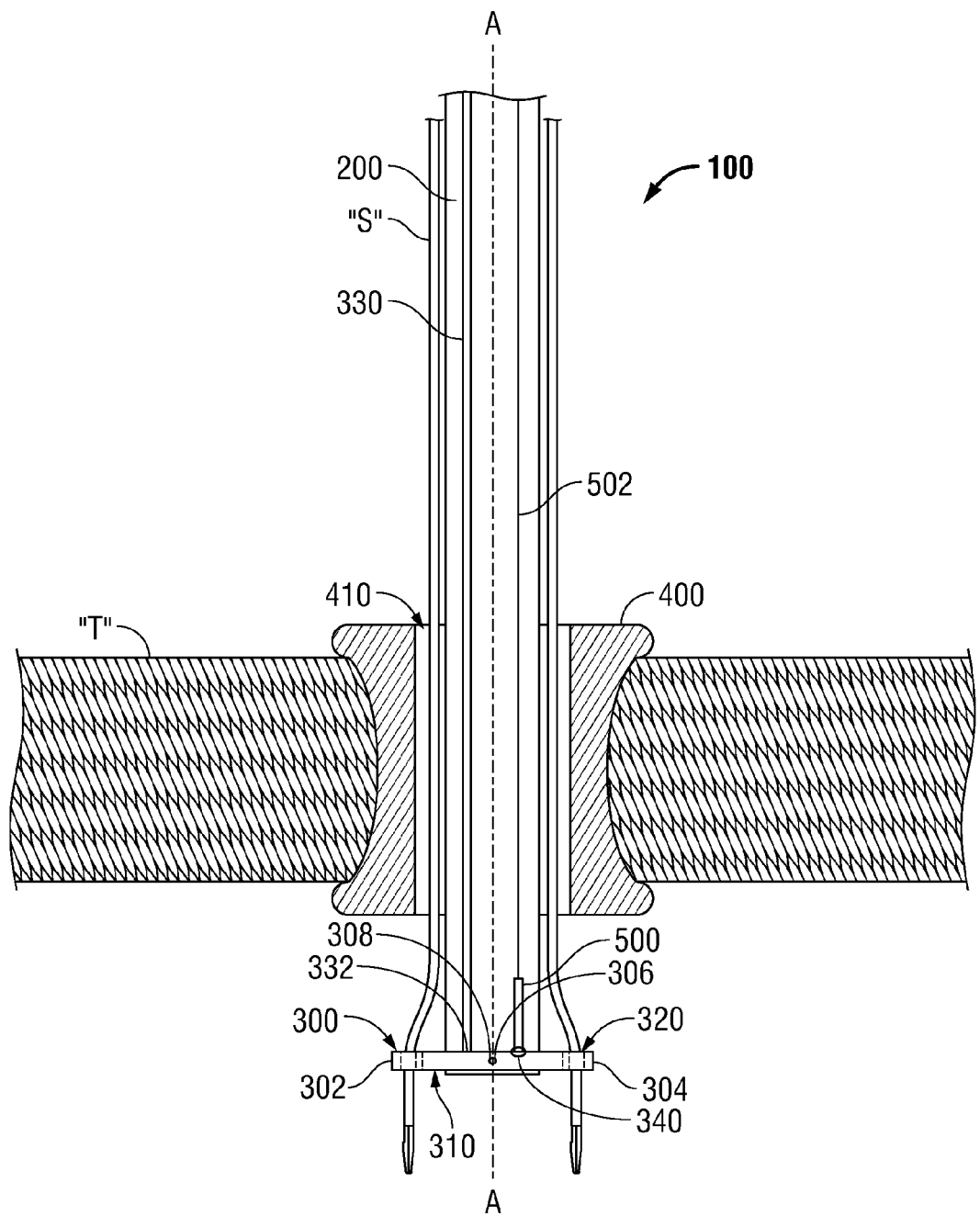
FIG. 10 is a side cut-away view of the surgical triangulation device of FIG. 9 further including a latch and a wire/rod.
Figure 11:
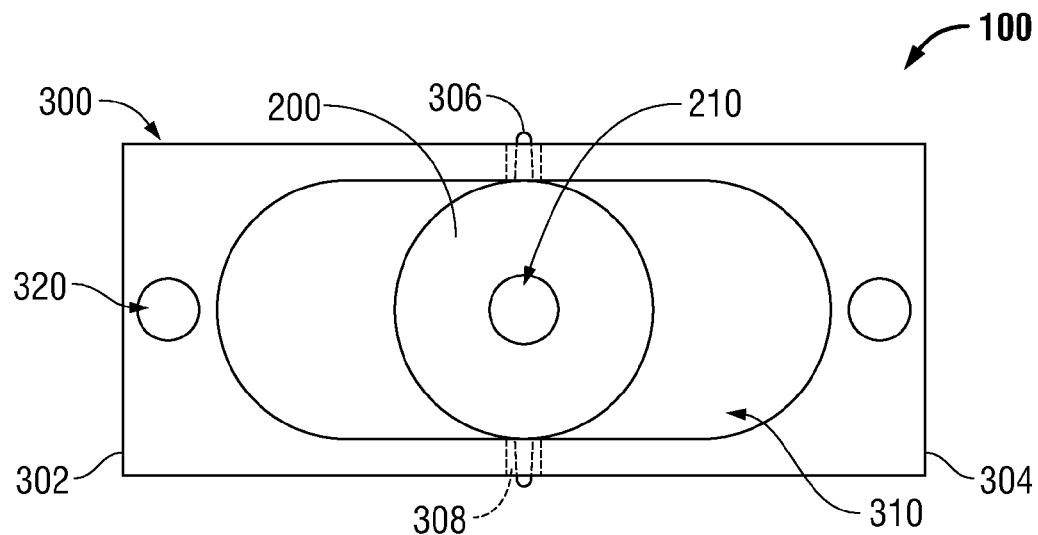
FIG. 11 is a bottom view of the surgical triangulation device of FIG. 1 when in the deployed position.
Figure 12:
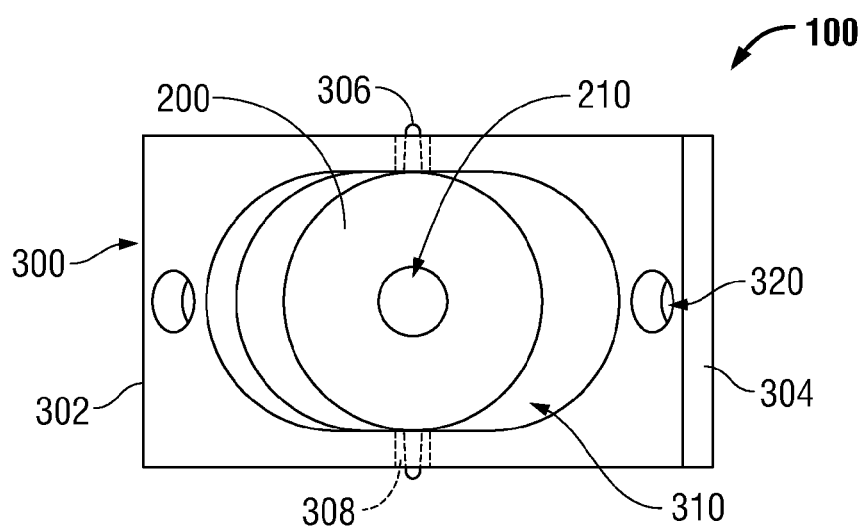
FIG. 12 is a bottom view of the surgical triangulation device of FIG. 1 when in the insertion position.

With further reference to FIG. 10, a latch 500 may be provided for securing platform 300 in the deployed position. Platform 300 may include a groove or detent 340 dimensioned to receive a portion of latch 500. Latch 500 may be actuated through the use of a wire or rod 502 and may include a spring loaded mechanism (not shown) where, when platform 300 pivots to the deployed position, latch 500 automatically slides into detent 340 to secure platform 300 in place. Platform 300 may then be unsecured by manipulating wire or rod 502 such that latch 500 is removed from detent 340, thereby allowing platform 300 to once again be pivoted.

Referring now to FIGS. 6-10, surgical portal apparatus 400 is shown. Surgical portal apparatus 400 is adapted for sealed insertion into an incision in tissue "T", or any naturally occurring opening, and includes at least one lumen 410 extending therethrough, where lumen 410 is adapted for the reception of surgical objects "S" and or surgical triangulation device 100 in a substantially sealed fashion. Surgical portal apparatus 400 may further include a valve or valves (not shown) disposed within lumen 410 for providing a fluid tight seal when surgical objects "S" are removed. It is contemplated that surgical access portal 400 may include additional lumens 420 adapted for the reception of surgical objects "S" in a substantially fluid sealed manner as will be further discussed below with reference to FIG. 13.

Figure 13:
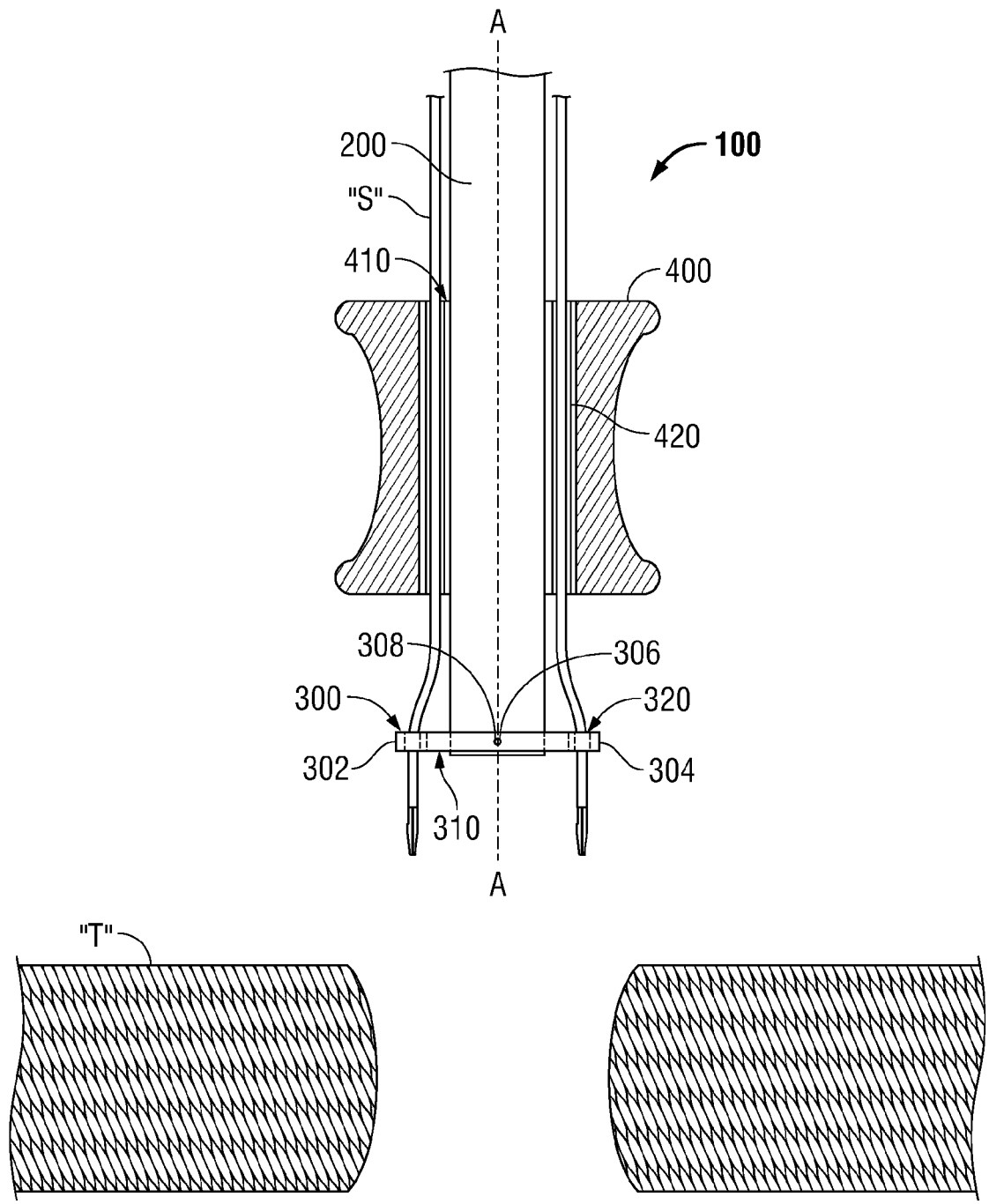
FIG. 13 is a side cut-away view of the surgical triangulation device of FIG. 1 inserted through a surgical access portal prior to insertion into an incision or orifice.

Referring now to FIG. 13, to better provide for a substantially fluid sealed surgical space, surgical triangulation device 100 and surgical objects "S" may be inserted through lumen 410 and side lumens 420 of surgical access portal 400, respectively, prior to the insertion of surgical access portal 400 into an incision in tissue "T" or other orifice. This allows surgical objects "S" to be individually fluid-sealed within each side lumen 420 such that when surgical access portal 400 and surgical triangulation device 100 are inserted into the incision in tissue "T" the surgical space is substantially fluid tight.

Figure 14:
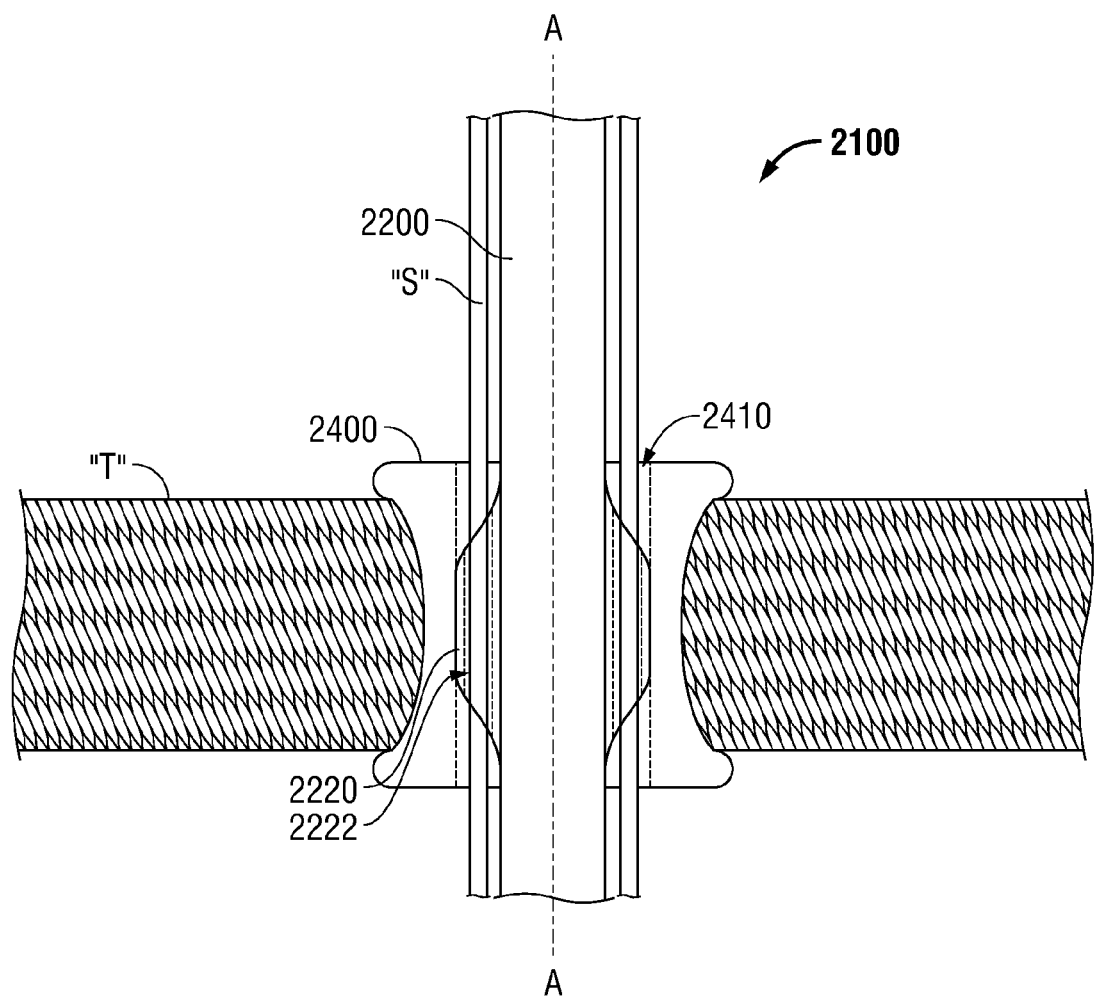
FIG. 14 is a side cut-away view of an alternate embodiment of a portion of the surgical triangulation device of FIG. 1.
Figure 15:
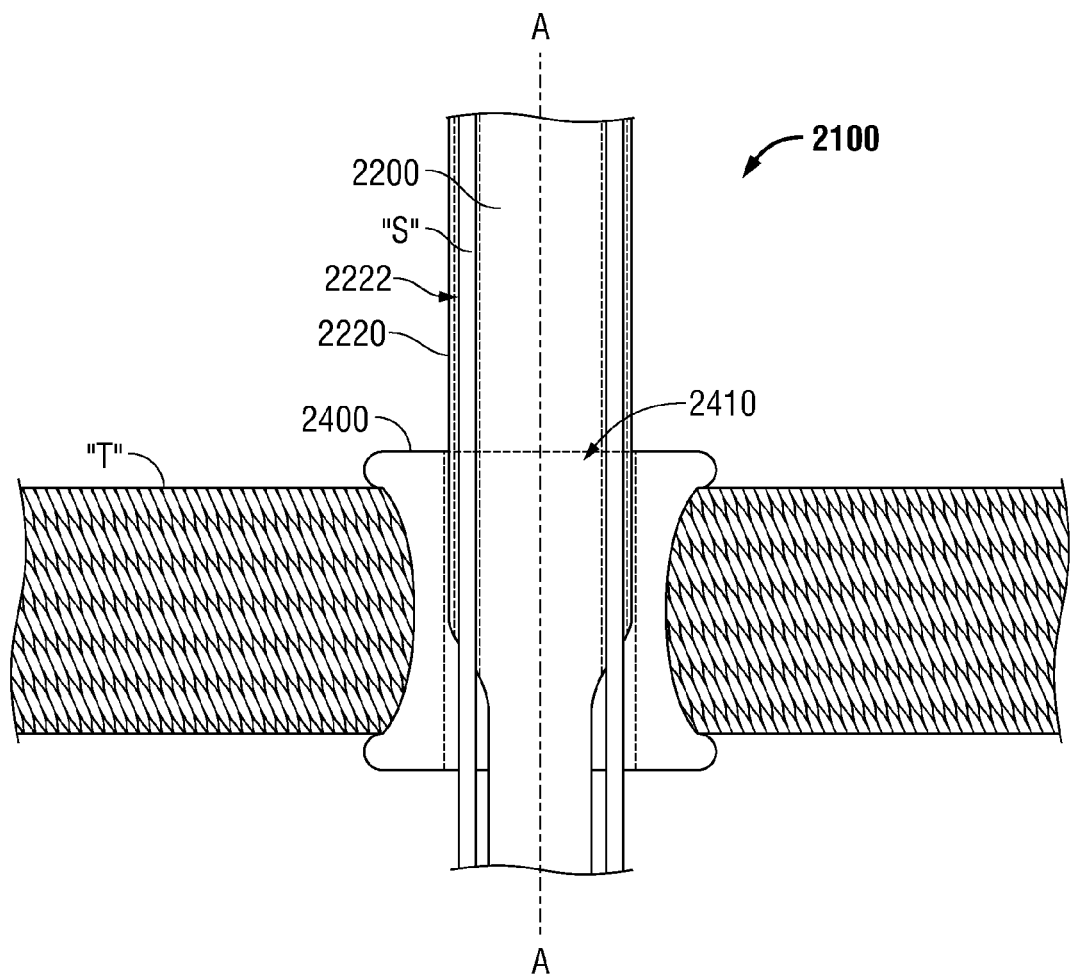
FIG. 15 is a side cut-away view of an alternate embodiment of a portion of the surgical triangulation device of FIG. 14.

Referring now to FIGS. 14 and 15, an alternate embodiment of surgical triangulation device 2100 is now disclosed including an elongate member 2200 having an enlarged portion 2220. Enlarged portion 2220 is disposed proximal of the distal end of elongate member 2200 and is adapted to create a fluid tight seal with surgical access portal 2400 when inserted therethrough. Enlarged portion 2220 may be dimensioned to be fully contained within surgical access portal 2400 when elongate member 2200 is inserted therethrough, as seen in FIG. 14, or may extend proximally (FIG. 15) or distally (not shown) out of either or both ends of surgical access portal 2400. Enlarged portion 2220 further includes a plurality of lumens 2222 adapted for the sealed reception of surgical objects "S" therethrough. Enlarged portion 2220 thus allows surgical triangulation device 2100 and surgical objects "S" to be inserted through a single lumen 2410 of surgical access portal 2400 while still maintaining a substantially fluid tight seal for insufflation purposes. In addition, surgical triangulation device 2100, including surgical objects "S", may be inserted through and removed from a single lumen 2410 of surgical access portal 2400 during surgery without necessitating the removal of surgical access portal 2400 from the incision or other orifice in the body. This allows other surgical instruments or devices to be inserted through or removed from the same lumen 2410 at different times during the course of a surgical operation.

In use, as shown by FIGS. 6-10, surgical triangulation device 100 is initially configured in the deployed position with platform 300 being orthogonal to longitudinal axis A-A. Surgical objects "S" are inserted through side lumens 320 to a preferred length. If locking member 322 is included the surgeon may secure surgical objects "S" in place by actuating locking member 322. The surgeon then manipulates one of surgical objects "S" or manipulates wire or rod 330 in a proximal or distal direction to transition platform 300 from the deployed position to the insertion position, where one of ends 302 or 304 abuts or is proximate to elongate member 200 and the other end 302 or 304 extends distally past elongate member 200. Once platform 300 is in the insertion position, where surgical triangulation device 100 defines a cross section only slightly larger than that of elongate member 200 alone, surgical triangulation device 100 is ready for insertion through lumen 410 of surgical access portal 400. Surgical access portal 400 may then be inserted into an incision in tissue "T". Alternatively surgical access portal 400 may have already been inserted into the incision in tissue "T" or surgical triangulation device 100 may be inserted through surgical access portal 400 prior to insertion of surgical access portal 400 into the incision in tissue "T" (FIG. 13). As discussed above with respect to FIG. 13, surgical objects "S" may be inserted through separate lumens 420 of surgical access portal 400 to assist in maintaining a fluid sealed surgical site. Once surgical access portal 400 is secured in the incision in tissue "T" or other orifice in the body, surgical triangulation device 100, if not already inserted, is inserted through lumen 410 and into the surgical site. The surgeon then manipulates one of surgical objects "S" or manipulates wire or rod 330 to transition platform 300 from the insertion position to the deployed position, where the deployed position is orthogonal to longitudinal axis A-A, the deployed position creates a separation or spacing between surgical objects "S" that are inserted through each of side lumens 320 and also between surgical objects "S" and elongate member 200. This allows a surgeon to approach the surgical site from different knowable angles and directions thereby allowing for triangulation of surgical objects "S". Upon reaching the deployed position, latch 500, if included, slides into detent 340 either automatically or through actuation of wire or rod 502 by the surgeon. Triangulation of surgical objects is now achieved and the surgeon may proceed with the surgery.

Once the surgery is complete, the surgeon manipulates wire or rod 502 to remove latch 500 from detent 340 and thereby allow platform 300 to pivot. The surgeon then manipulates surgical objects "S" or wire or rod 330 to transition platform 300 from the deployed position to the insertion position. Once in the insertion position surgical triangulation device 100 is removed from lumen 410 of surgical access portal 400 and surgical access portal 400 may then be removed from the incision. Alternatively, surgical access portal 400 may be removed from the incision or other orifice before removing surgical triangulation device 100 from surgical access portal 400.

Although the subject apparatus has been described with respect to preferred embodiments, it will be readily apparent, to those having ordinary skill in the art to which it appertains, that changes and modifications may be made thereto without departing from the spirit or scope of the subject apparatus.

The invention claimed is:

1. A surgical triangulation device comprising:
   an elongate member adapted for insertion through a surgical access portal and defining a longitudinal axis, the elongate member including at least one passage adapted for the reception of a first surgical object, and an open distal end in communication with the at least one passage; and
   a platform pivotably attached near a distal end of the elongate member and defining a plurality of lumens and a central opening therethrough, the central opening being configured to receive the open distal end of the elongate member such that the platform is pivotable between a first position, wherein a first end of the platform is positioned proximate to the elongate member and a second end of the platform extends distally past a distal end of the elongate member, and a second position, wherein the platform is nearly orthogonal to the longitudinal axis, the plurality of lumens being adapted for the reception of a second surgical object therethrough.

2. The surgical triangulation device of claim 1, wherein one or more of the plurality of lumens is disposed proximate to each of the first and second ends.

3. The surgical triangulation device of claim 1, wherein the central opening is dimensioned to allow a portion of the elongate member to project therethrough.

4. The surgical triangulation device of claim 1, wherein one or more of the plurality of lumens includes a locking member for securing a second surgical object thereto.

5. The surgical triangulation device of claim 4, wherein the platform is adapted to transition between the first and second positions upon actuation of a second surgical object.

6. The surgical triangulation device of claim 1, wherein the platform is adapted to transition between the first and second positions upon actuation of at least one actuating member attached thereto and extending proximally therefrom.

7. The surgical triangulation device of claim 6, wherein the at least one actuating member is at least one wire.

8. The surgical triangulation device of claim 6, wherein the at least one actuating member is a rod.

9. The surgical triangulation device of claim 1, wherein the elongate member further includes a latch disposed near the distal end and the platform further includes a detent dimensioned for reception of the latch, the latch and detent being adapted to secure the platform in the second position.

10. The surgical triangulation device of claim 9, wherein the latch is actuatable into and out of the detent by a cable or wire attached to the latch and extending proximally therefrom.

11. The surgical triangulation device of claim 9, wherein the latch is biased toward the detent by a spring-like mechanism.

12. The surgical triangulation device of claim 1, wherein a first surgical object is a scope.

13. The surgical triangulation device of claim 1, wherein the platform is orthogonal to the longitudinal axis when in the second position.

14. A surgical system comprising:
   a surgical access portal adapted for sealed insertion into an incision in tissue and defining at least one lumen therethrough; and
   a surgical triangulation device including an elongate member and a platform, the elongate member including at least one passage adapted for the reception of a surgical object, and an open distal end in communication with the at least one passage, the surgical triangulation device defining a longitudinal axis and being adapted for insertion through the at least one lumen of the surgical access portal, the platform pivotably attached near a distal end of the elongate member and defining a plurality of lumens and a central opening therethrough, the central opening being configured to receive the open distal end of the elongate member such that the platform is pivotable between a first position, wherein a first end of the platform is proximate to the elongate member and a second end of the platform extends distally past a distal end of the elongate member, and a second position, wherein the platform is nearly orthogonal to the elongate member.

* * * * *